Figure 1:
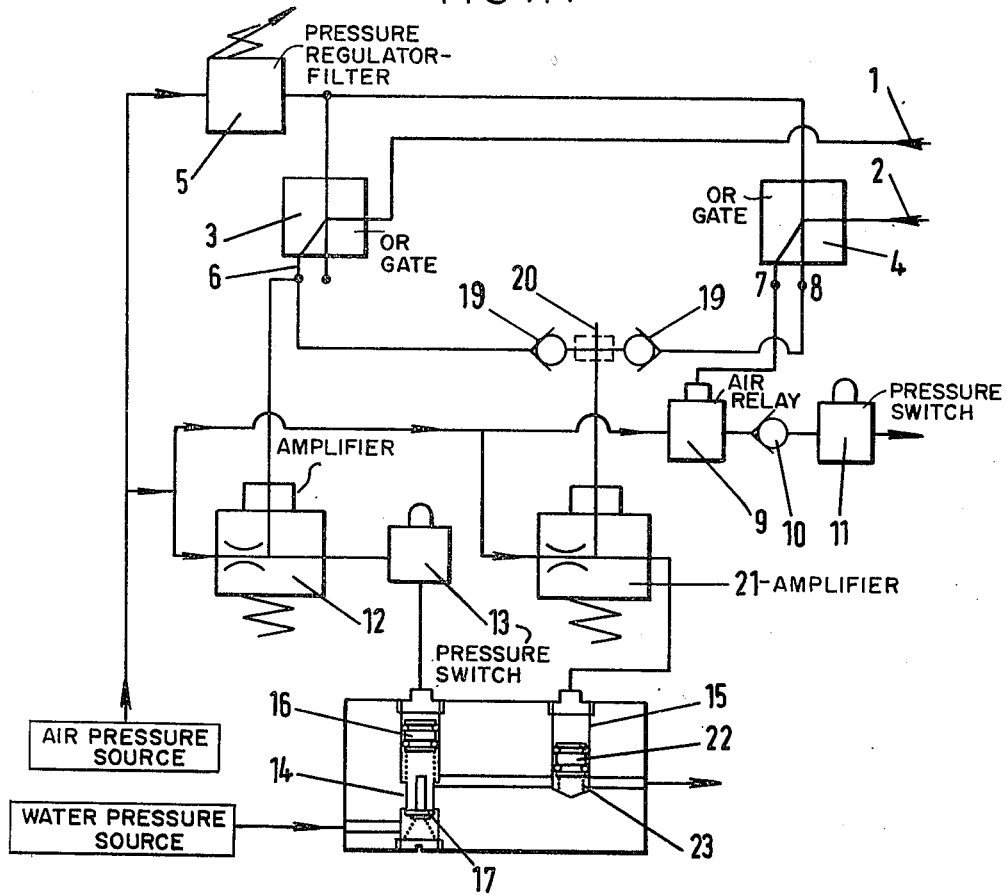

United States Patent [19]

Hill

[11] 3,971,375
[45] July 27, 1976

[54] DENTAL SYRINGE
[75] Inventor: Horace Kirby Hill, London, England
[73] Assignee: The Amalgamated Dental Company Limited, London, England
[22] Filed: Apr. 17, 1975
[21] Appl. No.: 569,329

[30] Foreign Application Priority Data
Apr. 19, 1974 United Kingdom............... 17333/74

[52] U.S. Cl............................. 128/173.1; 128/224; 32/28
[51] Int. Cl.² ....................................... A61M 11/00
[58] Field of Search................. 128/173.1, 173, 224, 128/230; 32/26, 27, 28; 239/398, 407

[56] References Cited
UNITED STATES PATENTS

| | | | |
|---|---|---|---|
| 3,129,511 | 4/1964 | Williams | 32/28 |
| 3,137,297 | 6/1964 | Maurer et al. | 128/173.1 |
| 3,254,646 | 6/1966 | Staunt et al. | 128/224 |
| 3,393,676 | 7/1968 | Kummer et al. | 128/173.1 |

*Primary Examiner*—John D. Yasko

[57] ABSTRACT

A dental syringe has a hand held unit coupled to a control unit and formed with air and water control apertures. An air pressure regulator is included in the control unit. The control unit has an air control fluid gate whose inputs are connected to the regulator and the air control aperture and whose output controls the supply of air to a nozzle. The control unit also has a water control fluid gate whose inputs are connected to the regulator and the water control aperture and whose output controls the supply of water to the nozzle.

10 Claims, 2 Drawing Figures

U.S. Patent July 27, 1976 3,971,375

DENTAL SYRINGE

This invention relates to a dental syringe connectable to sources of air and water under pressure and controllable to provide a flow of air or of water individually or to provide a simultaneous flow of air and water to form a spray.

Known dental syringes of this type have valves actuable by manually operable external levers. Because it is necessary to be able to produce a flow of water alone, a flow of air alone, and a spray consisting of water and air, the valves and their actuating mechanisms are generally quite complex. The complexity of the mechanisms has the effect that the syringe is not very robust and is liable to malfunction if mishandled, for example, if dropped.

It is an object of this invention to provide a dental syringe which is relatively robust.

According to this invention there is provided a dental syringe comprising a hand held syringe unit coupled to a control unit, the hand held syringe unit being formed with an air control aperture and a water control aperture, the control unit comprising an air pressure regulator intended to be connected to an air pressure source and arranged to produce a regulated air pressure output, an air control fluid gate having a control input connected to the air control aperture in the syringe unit, a fluid input connected to the output of the air pressure regulator and a fluid output the regulated air pressure being fed, in use, to the fluid output of the air control fluid gate only when the air control aperture is covered, an air control valve having a control input connected to the output of the air control fluid gate, an air input intended to be connected to the air pressure source, and an air output connected to an output nozzle in the syringe, the arrangement being that, when the regulated pressure appears at the output of the air control fluid gate, the air pressure source is connected to the said nozzle, a water control fluid gate having a control input connected to the water control aperture in the syringe unit, a fluid input connected to the output of the air pressure regulator, and a fluid output to which the regulated air pressure is applied, in use, only when the water control aperture is covered, and a water control valve having a water input intended to be connected to a water pressure source, a water output intended to be connected to the said nozzle, and a control input connected to the fluid output of the water control fluid gate.

Preferably the water control valve is arranged to suck back water when its control input ceases to receive fluid under pressure.

Suitably the water control valve comprises a valve seat, a valve member engageable with the valve seat to close the valve, a piston movable within a cylinder towards the valve member, and a spring which urges the piston away from the valve member, the control input of the water control valve communicating with the cylinder, the arrangement being that the application of fluid under pressure to the control input of the water control valve causes a force to be applied to the piston in the direction to urge it towards the valve member.

Preferably the air control fluid gate has a second fluid output to which, in use, the regulated air pressure is fed only when the air control aperture is uncovered, there being provided a fluid OR gate having first and second inputs connected respectively to the fluid output of the water control fluid gate and to the second fluid output of the air control fluid gate, and a fluid output, and a fluid controlled suction device intended to be connected to the nozzle, the suction device having a control input connected to the fluid output of the fluid OR gate, and arranged to suck back water from the nozzle when the air pressure at the fluid output of the fluid OR gate ceases.

Suitably the suction device comprises a water passage, a cylinder leading into the passage, a piston disposed in the cylinder and a spring which urges the piston out of the passage, the control input of the suction device communicating with the cylinder, the arrangement being that the application of fluid under pressure to the control input of the suction device causes a force to be applied to the piston in the direction to urge it into the passage.

Preferably the dental syringe comprises a fluid amplifier having a control input connected to the output of the fluid OR gate, a fluid input intended to be connected to the air pressure source, and a fluid output connected to the control input of the suction device.

Preferably the dental syringe comprises a fluid amplifier having a control input connected to the output of the water control fluid gate, a fluid input intended to be connected to the air pressure source, and a fluid output connected to the control input of the water control valve.

Preferably the dental syringe comprises a first pressure switch in the connection to the control input of the water control valve and a second pressure switch in series with the air output of the air control valve, both pressure switches being coupled to an electric switch which controls the energisation of a heater in the nozzle.

Figure 2:
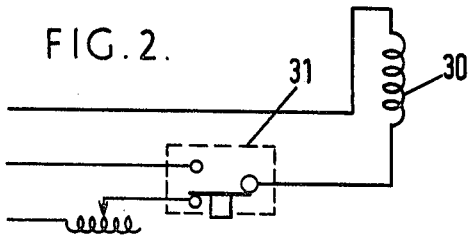

A dental syringe in accordance with this invention will now be described, by way of example only, with reference to the accompanying drawings of which:

FIG. 1 is a block diagram of the fluid control system of the dental syringe; and FIG. 2 is an electrical circuit diagram of the syringe.

The dental syringe is in two parts, that is, a hand held syringe unit connected to a control unit, which is normally fixed, by a lead having four passages.

The syringe has a water control aperture 1 and an air control aperture 2 connected to the control inputs of fluid gates 3 and 4 respectively.

A filter and regulator 5 intended to be connected to an air pressure source at, say, 40 p.s.i. produces a regulated pressure output at, say, 7 p.s.i. The filter and regulator 5 may, for example, include a 5 micron element. The regulated air pressure from the regulator 5 is applied the fluid inputs of the fluid gates 3 and 4. Each of the gates 3 and 4 has two outputs and has two control inputs so that it is an OR or NOR gate. However in each case only one control input is utilised and it is only that control input which is shown.

Each of the fluid gates has two outputs but in the case of the gate 3 only the output 6 is used, no pressure being present at output 6 when aperture 1 is uncovered but the regulated pressure being present at output 6 when aperture 1 is covered. Both outputs 7 and 8 of gate 4 are used, the regulated pressure being at the output 7 when the aperture 2 is covered and at the output 8 when the aperture 2 is uncovered.

A fluid controlled air relay 9 has its input connected to the air pressure source and has its output connected through a non-return valve 10 and a pressure switch 11 in series to the nozzle of the syringe. The control input of the relay 9 is connected to the output 7 of the gate 4. Connected to the output 8 of the gate 4 through a diode 18 is the control side of diaphragm amplifier 21 whose input is connected to the air pressure source. The output of the amplifier 21 is connected to an air controlled suction chamber 15 which is formed in the same block as an air controlled suck back valve 14 and connected in the line between the water pressure source and the nozzle of the syringe. Further connected to the control side of the amplifier 21 is a bleed hole 20 and diode 19 which is in turn connected to the output 6 of gate 3.

Whilst aperture 2 is uncovered the regulated air pressure appears at output 8 so that the amplifier 21 applies air under pressure to the air controlled suction chamber 15 which holds down piston 22. When aperture 2 is covered the regulated air pressure appears at output 7 which connectes relay 9 input and its output, and the air under pressure is applied through the non-return valve 10 and the pressure switch 11 to the syringe nozzle. The amplifier 21 is deactivated and piston 22 moves back under the action of a spring 23 to give a suction on the water line.

When both apertures are covered water and air are supplied together to provide a spray at the syringe nozzle. Although the aperture 2 is covered and no regulated air is flowing through diode 18 to amplifier 21 the amplifier 21 is kept activated by the regulated air flow from output 6 of the gate 3 through the diode 19.

The output 6 of the fluid gate 3 is applied to the control input of a diaphragm amplifier 12 whose input is connected to the air pressure source. The output of the amplifier 12 is connected through a pressure switch 13 to the control input of an air controlled suck back valve 14 connected in series and formed in the same block as an air controlled suction chamber 15. The valve 14 and suction chamber 15 are connected in the line between the water pressure source (say 25 p.s.i.) and the nozzle of the syringe.

When aperture 1 is covered the regulated air pressure appears at the output 6 so that the amplifier 12 applies air under pressure through the pressure switch 13 to the control input of the air controlled suck back valve 14 which activates piston 16 to travel and unseat valve 17 to allow water to flow through it. When aperture 1 is uncovered the regulated air pressure is cancelled at output 6 therefore deactivaing the air controlled suck back valve 14 allowing valve 17 to reseat under the action of a spring, and allowing piston 16 to travel back, under the action of a spring, thus creating a suck back action on the water line to the syringe.

It will be appreciated that the apertures 1 and 2 are so positioned in the hand held syringe unit as to be coverable by the dentist's fingers or thumb.

The syringe unit is relatively simple and therefore robust and includes an electrical heater 30 controlled by a micro change over switch 31. The switch 31 is movable between a first standby position (that shown) in which heater 30 is slightly energised to a position in which the heater 30 is substantially energised. The pressure switches 11 and 13 both operate switch 31.

I claim:

1. A dental syringe comprising a hand held syringe unit coupled to a control unit, the hand held syringe unit being formed with an air control aperture and a water control aperture, the control unit comprising an air pressure regulator intended to be connected to an air pressure source and arranged to produce a regulated air pressure output, an air control fluid gate having a control input connected to the air control aperture in the syringe unit, a fluid input connected to the output of the air pressure regulator and a fluid output, the regulated air pressure being fed to the fluid output of the air control fluid gate only when the air control aperture is covered, an air control valve having a control input connected to the output of the air control fluid gate, an air input intended to be connected to the air pressure source, and an air output connected to an output nozzle in the syringe, the arrangement being that, when the regulated pressure appears at the output of the air control fluid gate, the air pressure source is connected to the said nozzle, a water control fluid gate having a control input connected to the water control aperture in the syringe unit, a fluid input connected to the output of the air pressure regulator, and a fluid output to which the regulated air pressure is fed only when the water control aperture is covered, and a water control valve having a water input intended to be connected to a water pressure source, a water output connected to the said nozzle and a control input connected to the fluid output of the water control fluid gate.

2. A dental syringe as claimed in claim 1 wherein the water control valve acts to suck back water when its control input ceases to receive fluid under pressure.

3. A dental syringe as claimed in claim 2 wherein the water control valve comprises a valve seat, a valve member engageable with the valve seat to close the valve, a piston movable within a cylinder towards the valve member and a spring which urges the piston away from the valve member, the control input of the water control valve communicating with the cylinder, the arrangement being that the application of fluid under pressure to the control input of the water control valve causes a force to be applied to the piston in the direction to urge it towards the valve member.

4. A dental syringe as claimed in claim 3 wherein the water control valve comprises a further spring which urges the valve member towards the valve seat.

5. A dental syringe as claimed in claim 1 wherein the air control fluid gate has a second fluid output to which the regulated air pressure is fed only when the air control aperture is uncovered, there being provided a fluid OR gate having first and second inputs connected respectively to the fluid output of the water control fluid gate and to the second fluid output of the air control fluid gate, and a fluid output, and a fluid controlled suction device connected to the nozzle, the suction device having a control input connected to the fluid output of the fluid OR gate and arranged to suck back water from the nozzle when the air pressure at the fluid output of the fluid OR gate ceases.

6. A dental syringe as claimed in claim 5 wherein the suction device comprises a water passage, a cylinder leading into the passage, a piston disposed in the cylinder and a spring which urges the piston out of the passage, the control input of the suction device communicating with the cylinder, the arrangement being that the application of fluid under pressure to the control input of the suction device causes a force to be applied to the piston in the direction to urge it into the passage.

7. A dental syringe as claimed in claim 5 which comprises a fluid amplifier having a control input connected to the output of the fluid OR gate, a fluid input intended to be connected to the air pressure source, and a fluid output connected to the control input of the suction device.

8. A dental syringe as claimed in claim 3 wherein the air control fluid gate has a second fluid output to which the regulated air pressure is fed only when the air control aperture is uncovered, there being provided a fluid OR gate having first and second inputs connected respectively to the fluid output of the water control fluid gate and to the second fluid output of the air control fluid gate, and a fluid output, and a fluid controlled suction device connected to the nozzle, the suction device having a control input connected to the fluid output of the fluid OR gate and arranged to suck back water from the nozzle when the air pressure at the fluid output of the fluid OR gate ceases, and wherein the suction device is formed in the valve block of the water control valve.

9. A dental syringe as claimed in claim 1 which comprises a fluid amplifier having a control input connected to the output of the water control fluid gate, a fluid input intended to be connected to the air pressure source, and a fluid output connected to the control input of the water control valve.

10. A dental syringe as claimed in claim 1 which comprises a first pressure switch in the connection to the control input of the water control valve and a second pressure switch in series with the air output of the air control valve, both pressure switches being coupled to an electric switch which controls the energisation of a heater in the nozzle.

* * * * *